United States Patent [19]

Carini

[11] Patent Number: 5,137,902
[45] Date of Patent: Aug. 11, 1992

[54] 4-ALKYLIMIDAZOLE DERIVATIVES AND ANTI-HYPERTENSIVE USE THEREOF

[75] Inventor: David J. Carini, Wilmington, Del.

[73] Assignee: E. I. Du Pont de Nemours and Company, Wilmington, Del.

[21] Appl. No.: 650,258

[22] Filed: Feb. 4, 1991

Related U.S. Application Data

[63] Continuation-in-part of Ser. No. 552,637, Jul. 13, 1990.

[51] Int. Cl.$^5$ ............... C07D 403/10; A61K 31/415
[52] U.S. Cl. .................................. 514/381; 548/253
[58] Field of Search ....................... 548/253; 514/381

[56] References Cited

U.S. PATENT DOCUMENTS 4,880,804 11/1989 Carini et al. ............... 548/253 X
5,015,651 5/1991 Carini et al. ............... 548/253 X

FOREIGN PATENT DOCUMENTS 0291969 11/1988 European Pat. Off. ............ 548/252

Primary Examiner—David B. Springer

[57] ABSTRACT

Angiotensin II antagonist antihypertensive compounds such as

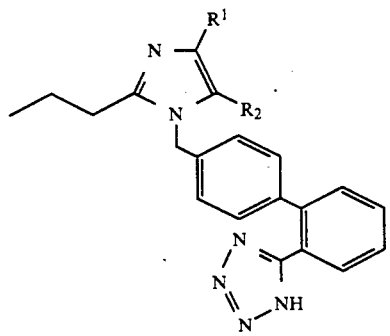

where $R^2$ is —CHO or —COOH and $R^1$ is ethyl have outstanding orally potency.

5 Claims, No Drawings

4-ALKYLIMIDAZOLE DERIVATIVES AND ANTI-HYPERTENSIVE USE THEREOF

RELATED APPLICATION

This application is a continuation-in-part of U.S. application Ser. No. 07/552,637, filed Jul. 13, 1990.

BACKGROUND OF THE INVENTION

Carini and Duncia, European Patent Application Publication Number (EPA) 0 253 310, published Jan. 20, 1988, discloses a class of imidazole angiotensin II antagonists useful for treatment of hypertension and congestive heart failure. The compounds are active when administered by intravenous injection. Several of the compounds are also orally active. The general disclosure encompasses certain 4-alkyl-2-propyl-1-[(2'-(1H-tetrazol-5-yl)biphenyl-4-yl)methyl]imidazoles substituted at the 5-position of the imidazole ring with halogen, nitro, trifluoromethyl or cyano.

Carini, Duncia and Wong, International Application Publication Number WO 89/06233, published Jul. 13, 1989, discloses the same class of imidazole angiotensin II antagonists and also discloses additional imidazole angiotensin II antagonists useful for treatment of hypertension and congestive heart failure. Some of the additionally-disclosed compounds are orally active. The general disclosure of WO 89/06233 encompasses the compounds of this invention, but the compounds of this invention are not specifically disclosed.

SUMMARY OF THE INVENTION

This invention is a class of 4-alkylimidazole compounds which exhibit remarkable and unexpected potency as antihypertensives in comparison to the compounds specifically disclosed in EPA 0 253 310 and WO 89/06233 which have been tested. The compounds of this invention are 4-alkyl-2-propyl-1-[(2'-(1H-tetrazol-5-yl)biphenyl-4-yl)methyl]imidazole-5-carboxaldehydes and -5-carboxylic acids which can be represented by formula I:

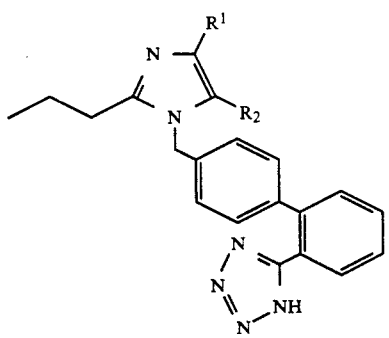

where:
R² is —CHO or —COOH; when R² is —CHO, R¹ is methyl, ethyl, i-propyl, or t-butyl; and when R² is —COOH, R¹ is ethyl, or i-propyl.

Most perferred because of outstanding oral antihypertensive potency are the compounds of formula I wherein R² is —CHO and R¹ is ethyl or t-butyl, and the compound of formula I wherein R² is —COOH and R¹ is ethyl.

The compounds of this invention which we have tested all have equal or greater oral antihypertensive potency than any of the compounds specifically disclosed in EPA 0 253 310 and WO 89/06233 which we have tested. The most preferred compounds of this invention exhibited oral antihypertensive activity approximately 2 to 4 fold higher than the most active compounds specifically disclosed EPA 0 253 310 and WO 89/06233 which have been tested.

The compounds of the invention are also highly active antihypertensive agents when administered by intravenous injection.

The invention includes a method of treating hypertension by orally administering a compound of formula I.

DESCRIPTION OF THE INVENTION

Synthesis

The compounds of Formula I can be prepared by the chemistry described in Scheme 1. The imidazole aldehydes (4) or imidazole esters (5) are allowed to react with an appropriately protected benzyl halide, tosylate, or mesylate (8: prepared as described in U.S. Pat. No. 4,820,843) in the presence of a base, potassium carbonate, etc., in a solvent such as dimethylformamide at 20°–100° C. for 1–48 hours. These alkylations produce a mixture of regioisomers in which the major product is the regioisomer corresponding to Formula I. Removal of the triphenylmethyl protecting-group with aqueous acids such as hydrochloric acid, followed, when appropriate, by saponification of the ester group with aqueous hydroxide, produces the compounds of this invention.

SCHEME 1

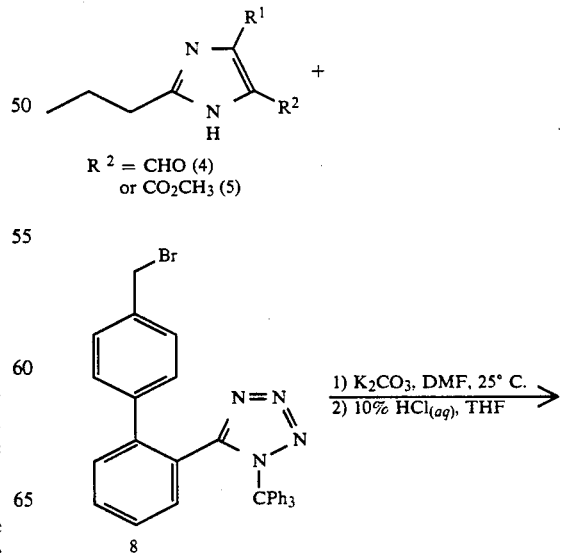

-continued
SCHEME 1 or aldehydes (4) to imidazole carboxylic acids followed by esterification of the acids (familiar to one skilled in the art); alternatively the aldehydes (4) can be oxidized directly to the esters (5) with $NaCN$/acetic acid/$MnO_2$ in methanol (Corey, et al., *J. Am. Chem. Soc.* (1968) 90, 5616).

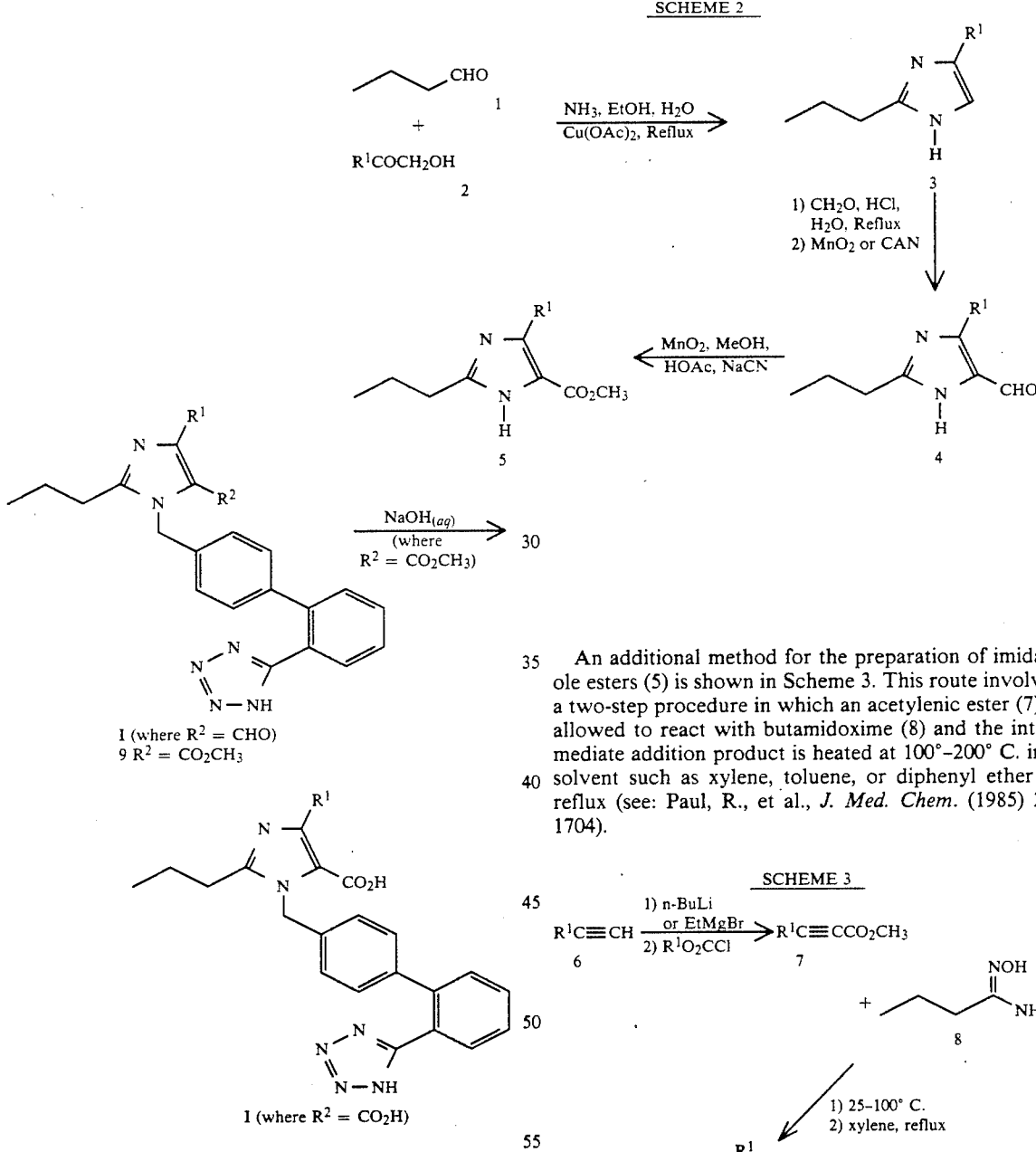

The intermediate aldehydes (4) and esters (5) can be prepared as described in Scheme 2. The dialkylimidazoles (3) are produced by the classic Weidenhagen imidazole synthesis. In this case an α-hydroxyketone (2) is treated with butyraldehyde (1) in the presence of copper (II) acetate and ammonia. Hydroxymethylation of the 3 is conducted employing formaldehyde and aqueous acid, as described by Kempe, et al., in U.S. Pat. No. 4,278,801. Oxidation of the intermediate hydroxymethylimidazoles with a reagent such as manganese dioxide or ceric ammonium nitrate (CAN) provides the desired aldehydes (4). The esters (5) can be prepared by oxidation of the hydroxymethylimidazoles An additional method for the preparation of imidazole esters (5) is shown in Scheme 3. This route involves a two-step procedure in which an acetylenic ester (7) is allowed to react with butamidoxime (8) and the intermediate addition product is heated at 100°-200° C. in a solvent such as xylene, toluene, or diphenyl ether at reflux (see: Paul, R., et al., *J. Med. Chem.* (1985) 28, 1704).

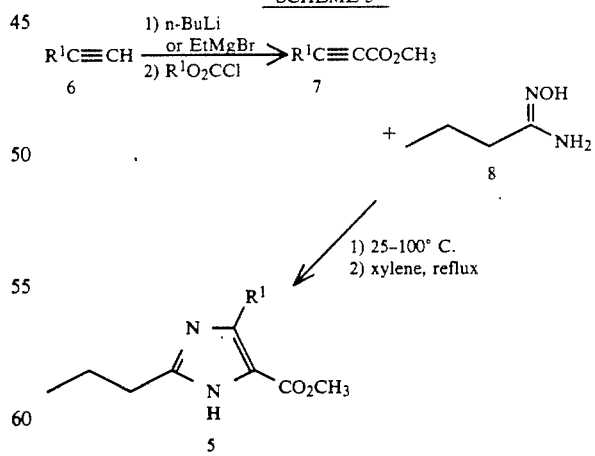

The compounds of this invention and their preparation can be understood further by the following examples, which do not constitute a limit of the invention. In these examples, unless otherwise indicated, all temperatures are in degrees centigrade and parts and percentages are by weight.

EXAMPLE 1

Part A: Preparation of 4(5)-Ethyl-2-propylimidazole

To a well-stirred mixture of 144 mL of butyraldehyde and 480 g of copper(II) acetate monohydrate in 2000 mL of 25% aqueous ammonia at 0° C. was added 82.4 mL of 1-hydroxy-2-butanone dropwise over 0.5 hour. The mixture then was heated to 80°-100° C. for 0.5 hour. After allowing the mixture to cool, the solvent was decanted, and the remaining materials were triturated with aqueous ethanol, the resulting gray-green solids were recovered by filtration.

Into a suspension of the above solids in water at 80° C. was bubbled hydrogen sulfide gas for 0.5 hour. The mixture then was filtered, while still hot, to remove the solid copper(I) sulfide. After cooling the filtrate was extracted with methylene chloride. The combined organic phases were washed with brine, dried over anhydrous sodium sulfate, filtered, and concentrated to furnish 10.1 g of the product as a viscous oil. A small sample of the product was recrystallized from 1-chlorobutane/hexane to afford a solid; mp 68.5°-70° C. the remaining crude product was employed in the subsequent reaction without further purification.

NMR (200 MHz, CDCl$_3$) $\delta$ 7.60 (br s, 1H), 6.64 (s, 1H), 2.61 (m, 4H), 1.73 (sext., 2H), 1.21 (t, 3H), 0.94 (t, 3H).

Part B: Preparation of 4(5)-Ethyl-5(4)-hydroxymethyl-2-propylimidazole

A solution of 10.0 g of 4(5)-ethyl-2-propylimidazole, 6.0 g of 37% aqueous formaldehyde, 32.5 g of concentrated hydrochloric acid, and 43 mL of water was refluxed for 65 hours. After cooling, the mixture was diluted with water, and the resulting solution was adjusted to pH 10 employing 10% aqueous sodium hydroxide and then was extracted with 4:1 chloroform/2-propanol. The combined organic phases were washed with brine, dried over anhydrous sodium sulfate, filtered, and concentrated. Column chromatography on silica gel (elution: 10% methanol/chloroform with 0.2% conc. amonia) followed by recrystallization from ethyl acetate provided 5.86 g of the product; mp 159°-160° C.

NMR (200 MHz, DMSO-d$_6$) $\delta$ 11.28 (br s, 1H), 4.62 (br s, 1H), 4.26 (s, 2H), 2.47 (m, 4H), 1.61 (sext, 2H), 1.09 (t, 3H), 0.88 (t, 3H).

Part C: Preparation of 4(5)-Ethyl-2-propylimidazole-5(4)-carboxaldehyde

To a solution of 5.60 g of 4(5)-ethyl-5(4)-hydroxymethyl-2-propylimidazole in 85 mL of glacial acetic acid at 25° C. was added 72 mL of 1.0N ceric ammonium nitrate/water dropwise over 1.0 hour. The resulting solution was stirred at 25° C. for 1.0 hour and then was poured into water. This solution was adjusted to ~pH 5 employing aqueous sodium hydroxide (~0.9 eq added based on acetic acid used above) and then was extracted with chloroform. The combined organic phases were washed with water (2×) and brine, dried over anhydrous sodium sulfate, filtered, and concentrated to afford 3.70 g of the product as a yellow oil.

NMR (200 MHz, CDCl$_3$) $\delta$ 9.66 (s, 1H), 2.93-2.73 (m, 4H), 1.79 (sext, 2H), 1.32 (t, 3H), 0.96 (t, 3H).

Part D: Preparation of 4-Ethyl-2-propyl-1-[(2'-(1H-tetrazol-5-yl)biphenyl-4-yl)methyl]imidazole-5-carboxaldehyde A solution of 1.76 g of 4(5)-ethyl-2-propylimidazole-5(4)-carboxaldehyde, 2.95 g of anhydrous potassium carbonate, 6.95 g of 4'-bromomethyl-2-((triphenylmethyl)tetrazol-5-yl)biphenyl (~85% purity, prepared as described in U.S. Pat. No. 4,820,843), and 30 mL of dimethylformamide was stirred at 25° C. for 22 hours. The reaction mixture was filtered, and the filtrate was concentrated under vacuum; the residue was diluted with water and extracted with ethyl acetate. The combined organic phases were washed with water and brine, dried over anhydrous sodium sulfate, filtered, and concentrated. Column chromatography on silica gel (elution: ethyl acetate/ benzene) furnished 3.79 of the alkylation product as an oil.

A solution of 2.00 g of the alkylation product in 25 mL of 10% aqueous hydrochloric acid and 50 mL of tetrahydrofuran was stirred at 25° C. for 18 hours. To the reaction was added excess aqueous sodium hydroxide, and the solvents then were removed under vacuum. The residue was dissolved in water, and the solution was filtered to remove the triphenylmethanol. The filtrate was adjusted to pH 3-3.5 employing 10% hydrochloric acid. The resulting suspension was stirred for several hours, and then the solids were recovered by filtration and dried to provide 0.97 g of the product as an amorphous white solid.

NMR (200 MHz, DMSO-d$_6$) $\delta$ 16.30 (br s, 1H), 9.77 (s, 1H), 7.72-7.51 (m, 4H), 7.02 (A$_2$B$_2$, 4H), 5.57 (s, 2H), 2.81 (quart, 2H), 2.57 (t, 2H), 1.57 (sext, 2H), 1.23 (t, 3H), 0.86 (t, 3H).

EXAMPLE 2

Part A: Preparation of Methyl 4(5)-ethyl-2-propylimidazole-5(4)-carboxylic acid A mixture of 4.24 g of methyl 2-pentynoate and 4.41 g of butamidoxime was stirred at 25° C. for 18 hours. Column chromatography on silica gel (elution: 0-10% methanol/methylene chloride) furnished 1.03 g of an oil. A solution of this oil in xylene was refluxed for 24 hours. After cooling, the solvent was removed under vacuum, and the residue was chromatographed on silica gel (elution: 0-5% methanol/methylene chloride) to afford 0.41 g of the product as a waxy solid.

NMR (300 MHz, CDCl$_3$) $\delta$ 3.87 (s, 3H), 2.62 (t, 2H), 1.81-1.61 (m, 4H), 1.24 (t, 3H), 0.94 (t, 3H).

Part B: Preparation of Methyl 4-ethyl-2-propyl-1-[(2'-(1H-tetrazol-5-yl)biphenyl-4-yl)methyl]imidazole-5-carboxylic acid The title compound was prepared from methyl 4(5)-ethyl-2-propyl-imidazole-5(4)-carboxylic acid according to the procedure described in Example 1, Part D.

NMR (300 MHz, CDCl$_3$) $\delta$ 7.74 (m, 1H), 7.50-7.23 (m, 3H), 7.03 (d, 2H), 6.86 (d, 2H), 5.60 (s, 2H), 3.83 (s, 3H), 3.00-2.86 (m, 4H), 1.71-1.66 (m, 2H), 1.25 (t, 3H), 0.83 (t, 3H).

Part C: Preparation of 4-Ethyl-2-propyl-1-[(2'-(1H-tetrazol-5-yl)biphenyl-4-yl)methyl]imidazole-5-carboxylic acid A solution of 0.61 g of methyl 4-ethyl-2-propyl-1-[(2'-(1H-tetrazol-5-yl)-biphenyl-5-yl)methyl]imidazole-5-carboxylic acid, 5 mL of 5% aqueous sodium hydroxide, 5 mL of methanol, and 15 mL of tetrahydrofuran was refluxed for 120 hours. After cooling, the solvents were removed under vacuum, and the residue was dissolved in 100 mL of water. The solution was adjusted to pH 4 employing 10% hydrochloric acid and then was extracted with 4:1 methylene chloride/2-propanol. The combined organic phases were dried over anhydrous sodium sulfate, filtered, and concentrated under vacuum to provide 0.41 g of the product as a glassy solid.

NMR (300 MHz, CDCl$_3$) δ 7.71-7.51 (m, 4H), 7.08 (m, 4H), 5.73 (s, 2H), 2.96 (quart, 2H), 2.84 (t, 2H), 1.54 (m, 2H), 1.21 (t, 3H), 0.84 (t, 3H).

Examples 3-15 (Table 1) can be or have been prepared according to the procedures described in Examples 1 and 2.

TABLE 1

| Example | R$^1$ | R$^2$ | NMR (300 MHz) |
|---|---|---|---|
| 3 | methyl | CHO | a |
| 4 | tert-butyl | CHO | b |
| 5 | iso-propyl | CHO | |
| 6 | iso-propyl | CO$_2$H | | a NMR (DMSO-d$_6$) δ 9.75 (s, 1H), 7.71-7.50 (m, 4H), 7.02 (A$_2$B$_2$, 4H), 5.55 (s, 2H), 2.55 (t, 2H), 2.40 (s, 3H), 1.56 (sext, 2H), 0.84 (t, 3H).

b NMR (CDCl$_3$) δ 10.13 (s, 1H), 7.99 (d, 1H), 7.51 (m, 2H), 7.41 (m, 1H), 7.14 (d, 2H), 6.96 (d, 2H), 5.60 (s, 2H), 2.81 (m, 2H), 1.73 (m, 2H), 1.50 (s, 9H), 0.95 (t, 3H).

Dosage Forms

The compounds of this invention can be administered for the treatment of hypertension by any means that effects contact of the active ingredient compound with the site of action in the body of a warm-blooded animal. For example, administration can be parenteral, i.e., subcutaneous, intravenous, intramuscular, or intraperitoneal. Preferably, administration is by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment, and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The active ingredient can be administered orally in solid dosage forms, such as capsules, tablets, and powders, or in liquid dosage forms, such as elixirs, syrups, and suspension. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated for film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol., a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

Claims:

1. An antihypertensive compound of the formula:

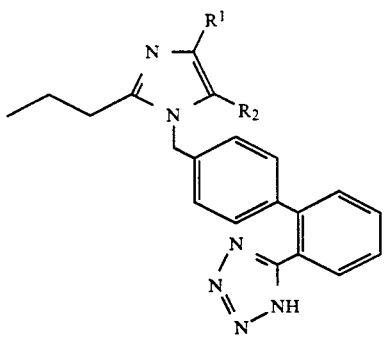

where
 $R^2$ is —CHO or —COOH;
 when $R^2$ is —CHO, $R^1$ is methyl, ethyl, i-propyl, or t-butyl; and
 when $R^2$ is —COOH, $R^1$ is ethyl, or i-propyl.

2. The compound of claim 1 wherein $R^2$ is —CHO and $R^1$ is ethyl.

3. The compound of claim 1 wherein $R^2$ is —CHO and $R^1$ is t-butyl.

4. The compound of claim 1 wherein $R^2$ is —COOH and $R^1$ is ethyl.

5. A method of treating hypertension in a warm-blooded animal comprising orally administering to the animal a compound of claim 1 in an amount effective to lower the animal's blood pressure.

* * * * *